US00PP21100P3

(12) United States Plant Patent
Andrusiv

(10) Patent No.: US PP21,100 P3
(45) Date of Patent: Jun. 29, 2010

(54) *BERBERIS* PLANT NAMED 'FIREBALL'

(50) Latin Name: *Berberis thunbergii*
Varietal Denomination: FIREBALL

(76) Inventor: Michal Andrusiv, J. Metyee 1078, Litoroyal (CZ) CZ 570 01

( * ) Notice: Subject to any disclaimer, the term of this patent is extended or adjusted under 35 U.S.C. 154(b) by 0 days.

(21) Appl. No.: 12/380,311

(22) Filed: Feb. 25, 2009

(65) Prior Publication Data

US 2009/0235416 P1 Sep. 17, 2009

(51) Int. Cl.
*A01H 5/00* (2006.01)

(52) U.S. Cl. ..... Plt./241

(58) Field of Classification Search ..... Plt./241
See application file for complete search history.

*Primary Examiner*—Susan B McCormick Ewoldt

(57) ABSTRACT

A new cultivar of *Berberis* plant named 'FIREBALL' that is characterized by semi prostrate habit and bright red foliage. In combination these traits set 'FIREBALL' apart from all other existing varieties of *Berberis* known to the inventor.

1 Drawing Sheet

Genus:*Berberis.*
Species: *thunbergii.*
Denomination: 'FIREBALL'.

BACKGROUND OF THE INVENTION

This application claims the benefit of priority under 35 U.S.C. 119(f) of the earlier-filed application for European Community Plant Breeders Rights, Application Number 2008/0457, filed Feb. 27, 2008.

The present invention relates to a new and distinct cultivar of barberry that is grown as a dwarf shrub for container or landscape. The new cultivar is known botanically as *Berberis thunbergii* and will be referred to hereinafter by the cultivar name 'FIREBALL'.

'FIREBALL' was selected by the inventor in Litomysl, The Czech Republic in 1994, for unique foliage color. The new cultivar 'FIREBALL' is a hybrid plant that resulted from deliberate cross-pollination conducted by the inventor in a cultivated area of Litomysl, The Czech Republic. Cross-pollination was between an individual plant of *Berberis thunbergii* 'Goldalita' (unpatented) and an individual plant of *Berberis thunbergii* 'Atropurpurea Nana' (unpatented). The female parent is *Berberis thunbergii* 'Goldalita' and the male parent is *Berberis thunbergii* 'Atropurpurea Nana'.

'FIREBALL' is a deciduous dwarf shrub whose foliage is bright red when exposed to direct sun. This foliage color persists throughout the summer season. There are no dwarf *Berberis* known to the inventor that exhibit this foliage color. To date the inventor has observed no flowers produced by 'FIREBALL'. The foliage color distinguishes 'FIREBALL' from all other *Berberis* known to the inventor.

'FIREBALL' differs from the parent plants as follows: Whereas the foliage of 'FIREBALL' is bright red, the foliage of the female parent plant 'Goldalita' is yellow; and the foliage of the male parent 'Atropurpurea Nana' is deep reddish brown.

The variety of *'Berberis'* which the inventor considers to most closely resemble 'FIREBALL' is *Berberis thunbergii* 'Bagatelle' (unpatented). Whereas the plant habit of 'Bagatelle' is similar to 'FIREBALL', the foliage of 'Bagatelle' is dull reddish-brown in color.

The first asexual reproduction of 'FIREBALL' was conducted by the inventor in 1995, in a cultivated area of Litomysl, The Czech Republic. The method used for asexual propagation was vegetative cuttings. Since that time the distinguishing characteristics of 'FIREBALL' have been determined stable and have reproduced true to type in successive generations.

SUMMARY OF THE INVENTION

The following traits have been repeatedly observed and represent the characteristics of the new *Berberis* cultivar 'FIREBALL'. These traits in combination distinguish 'FIREBALL' from all other commercial varieties of *Berberis* known to the inventor. 'FIREBALL' has not been tested under all possible conditions and phenotypic differences may be observed with variations in environmental, climatic and cultural conditions, without however, any variance in genotype.

1. *Berberis* 'FIREBALL' is a deciduous shrub.
2. *Berberis* 'FIREBALL' is suitable for use in containers or the landscape.
3. To date *Berberis* 'FIREBALL' has not produced flowers.
4. *Berberis* 'FIREBALL' exhibits a semi prostrate habit.
5. *Berberis* 'FIREBALL ' exhibits red foliage.
6. *Berberis* 'FIREBALL' is propagated using vegetative cuttings.
7. *Berberis* 'FIREBALL' is hardy to USDA Zone 5.
8. At maturity, *Berberis* 'FIREBALL' achieves width of 50 cm width and height of 50 cm.

BRIEF DESCRIPTION OF THE DRAWING

The accompanying color drawing illustrates an entire plant of 'FIREBALL' from a side perspective. The drawing was made in late summer. The illustrated plant is two years old and is planted in a 2 liter container. The plant has been grown out-of-doors in Boskoop, The Netherlands. Daytime temperatures ranged from 15° Centigrade to 30° Centigrade. Nighttime temperatures ranged from 7° Centigrade to 14° Centigrade. The light was normal outdoor light level. No photoperiodic treatments and no growth retardants were applied to the plants. Colors in the drawings may differ from the color values cited in the detailed botanical description, which accurately describe the actual colors of the new variety of *Berberis* named 'FIREBALL'.

BOTANICAL DESCRIPTION OF THE PLANT

Figure 1:
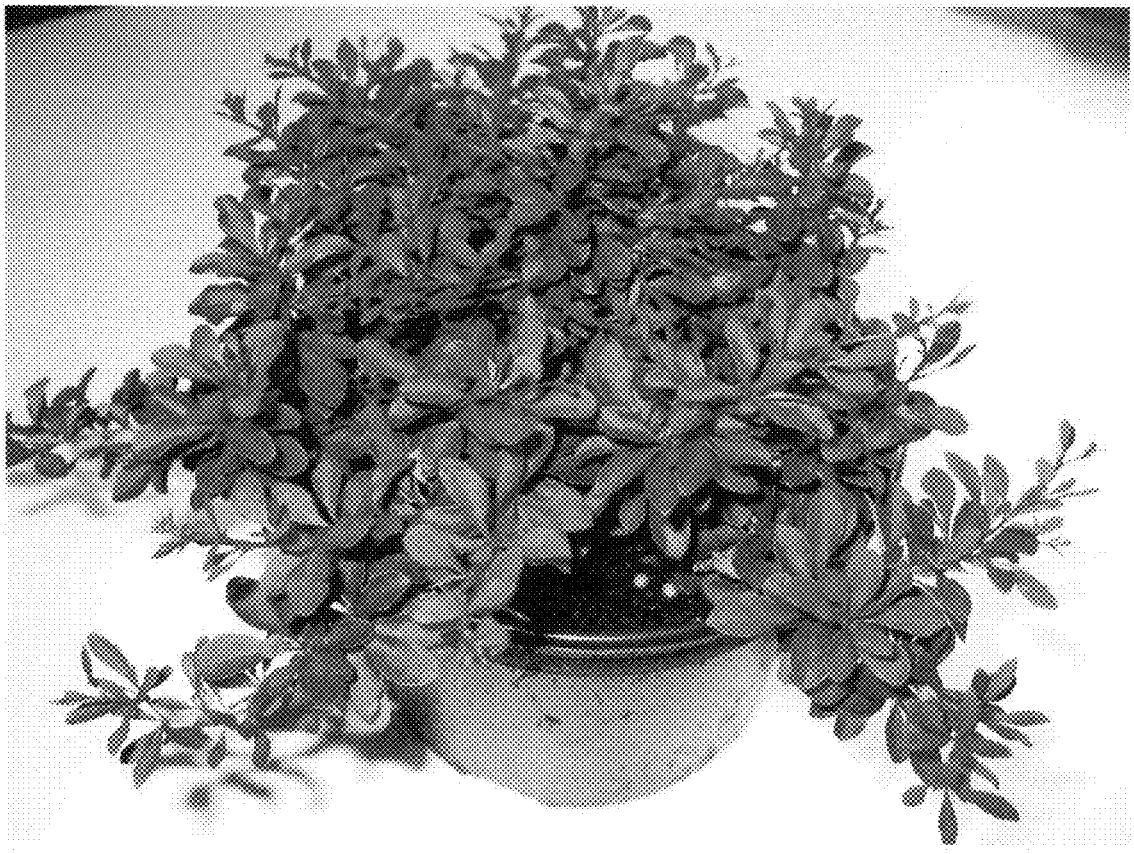

The following is a detailed description of 'FIREBALL' as grown in a 2-litre containers, out-of-doors in Boskoop, The Netherlands. The color determinations are in accordance with The 2002 Royal Horticultural Society Colour Chart of The Royal Horticultural Society, London, England, except where general color terms of ordinary dictionary significance are used. The growing requirements are similar to the species.

Botanical classification:

*Genus.*—*Berberis.*

*Species.*—*thunbergii.*

*Denomination.*—'FIREBALL'.

Commercial classification: Deciduous shrub.

Use: Plant for use in containers or landscape.

Common name: Barberry.

Commercial container size: For liner production, a 5 cm round or square plug or cell or container; for planting in the garden or landscape, a "nursery 1 gallon" or equivalent or larger.

Cultural requirements: Plant in full sun to light shade in well-drained soil with moderate to regular water.

Parentage: *Berberis* 'FIREBALL' is a hybrid plant that resulted from deliberate cross-pollination of the following parents:

*Female parent plant.*—An individual plant of *Berberis thunbergii* 'Goldalita'.

*Male parent plant.*—An individual plant of *Berberis thunbergii* 'Atropurpurea Nana'.

Plant description:

*Bloom period.*—None. Plant has not bloomed to date.

*Plant habit.*—Semi-prostrate: width similar to or slightly greater than height.

*Overall plant shape.*—Flattened globular.

*Vigor.*—Low to moderate vigor.

*Root system.*—Fibrous roots.

*Plant dimensions.*—2-liter container: 35 cm in width and 25 cm in height. At maturity: 50 cm. in width and 50 cm. in height.

*Growth rate.*—An average of 6 cm. per season until mature.

*Hardiness.*—USDA Zone 5.

*Propagation.*—Propagation is accomplished using vegetative cuttings.

*Rooting time.*—An average of 6 weeks is needed for an initial cutting to develop roots.

*Crop time.*—24 months are needed to produce a commercial 2-litre container from a rooted cutting.

*Special growing considerations.*—Pinching back improves branching.

*Disease resistance and susceptibility.*—Not more susceptible to pests and diseases than other *Berberis thunbergii* cultivars known to the inventor.

*High temperature tolerance.*—Not tested in higher however it is likely to be tolerant of temperatures up to 35° Centigrade.

Stem:

*Stem color* (*immature stems*).—N144A.

*Stem color* (*mature stems*).—200C.

*Stem shape.*—Cylindrical.

*Stem surface.*—Mature stems are slightly ribbed while immature stems are glabrous and glossy.

*Stem strength.*—Moderate in strength.

*Stem pubescence.*—None present.

*Basal stem dimensions.*—5 cm. in length and 0.5 cm. in diameter.

*Internode length.*—0.5cm-1.5cm. between nodes.

*Branching habit.*—Basal branching with free branching lateral stems.

*Number of lateral branches.*—An average of 80 lateral branches.

*Lateral branch length.*—An average of 8 cm. in length.

*Lateral branch diameter.*—An average of 1.2 mm. in diameter.

*Stipules, tendrils, thorns or spines.*—Thorns present.

*Thorn length.*—Thorns range in length from 4–6 mm and have basal diameter of 1 mm.

*Thorn apex.*—Acuminate.

*Thorn surface.*—Glabrous.

*Thorn base.*—Truncate.

*Thorn color.*—46C.

Foliage:

*Type.*—Deciduous.

*Arrangement.*—Alternate.

*Durability of leaf to stress.*—Moderate to high.

*Shape.*—Obovate.

*Margins.*—Entire.

*Division.*—Simple.

*Apex.*—Individual leaf apices range from mucronulate to abruptly acute.

*Base.*—Elongated attenuate.

*Pubescence* (*adaxial and abaxial surfaces*).—None present.

*Leaf surface* (*abaxial and adaxial surfaces*).—Glabrous.

*Leaf appearance* (*adaxial and abaxial surfaces*).—Slightly glossy.

*Quantity of leaves per lateral branch.*—An average of 50 leaves per lateral branch.

*Leaf length.*—Individual leaves are an average of 1.5 cm. in length.

*Leaf width.*—Individual leaves are an average of 0.8 cm. in width.

*Leaf attachment.*—Sessile.

*Petioles.*—None present.

*Leaf color when exposed to full sun* (*both surfaces*).—Ranges from 46D at palest, through 46C as predominant color, aging to 53B.

*Leaf color in shade or if leaf is obscured by foliage above.*—Ranges between N144A and 144A with patches of grayed-purple 184C to 184A.

*Venation.*—Pinnate.

*Vein color.*—Identical to lamina.

Flowers, reproductive organs and seed: None observed to date.

The invention claimed is:

1. A new and distinct cultivar of *Berberis* plant named 'FIREBALL' as described and illustrated herein.

* * * * *